US007472028B2

(12) United States Patent
Foote (10) Patent No.: US 7,472,028 B2
(45) Date of Patent: Dec. 30, 2008

(54) SENSOR OR CAPACITANCE MEASURING WITH A MICROPROCESSOR

(75) Inventor: Steve R. Foote, Bartlett, TN (US)

(73) Assignee: Kele Inc., Bartlett, TN (US)

( * ) Notice: Subject to any disclaimer, the term of this patent is extended or adjusted under 35 U.S.C. 154(b) by 568 days.

(21) Appl. No.: 11/158,393

(22) Filed: Jun. 21, 2005

(65) Prior Publication Data

US 2006/0006883 A1     Jan. 12, 2006

Related U.S. Application Data

(60) Provisional application No. 60/583,159, filed on Jun. 25, 2004.

(51) Int. Cl.
*G01R 25/00* (2006.01)

(52) U.S. Cl. ........................................ 702/65; 324/519

(58) Field of Classification Search ................... 702/57, 702/64–65, 138, 141, 150, 189, 198; 73/335.04, 73/780, 862.22, 862.337; 324/519, 658, 324/660–661, 686
See application file for complete search history.

(56) References Cited

U.S. PATENT DOCUMENTS

| | | | | |
|---|---|---|---|---|
| 4,065,715 A | * | 12/1977 | Jaffe et al. | ................... 324/678 |
| 4,465,229 A | | 8/1984 | Kompelien | |
| 4,504,922 A | * | 3/1985 | Johnson et al. | ............. 702/133 |
| 4,558,274 A | | 12/1985 | Carusillo | |
| 4,563,634 A | | 1/1986 | Lehle | |
| 4,661,768 A | | 4/1987 | Carusillo | |
| 4,831,325 A | | 5/1989 | Watson, Jr. | |
| 4,853,693 A | | 8/1989 | Eaton-Williams | |
| 5,027,077 A | | 6/1991 | Yanagisawa et al. | |
| 5,235,267 A | | 8/1993 | Schöneberg et al. | |
| 5,274,334 A | | 12/1993 | Mills | |
| 5,351,519 A | * | 10/1994 | Kress | .......................... 73/1.39 |
| 5,406,137 A | | 4/1995 | Scheler et al. | |
| 5,621,669 A | * | 4/1997 | Bjornsson | ..................... 702/85 |
| 5,841,641 A | * | 11/1998 | Faulk | ....................... 363/21.14 |
| 5,922,939 A | | 7/1999 | Cota | |
| 5,933,102 A | | 8/1999 | Miller et al. | |
| 5,973,417 A | | 10/1999 | Goetz et al. | |
| 6,230,543 B1 | | 5/2001 | Froehling et al. | |

(Continued)

OTHER PUBLICATIONS

Precise Impedance Measurement of Electrical Components Mar. 30, 2005 [http://www.cy-sensors.com/Impedance.htm].

*Primary Examiner*—Eliseo Ramos Feliciano
*Assistant Examiner*—Mary C Baran
(74) *Attorney, Agent, or Firm*—Bryan Cave LLP (57) ABSTRACT

An apparatus, system, and method for measuring parameters, measuring or determining capacitance, producing a digital output that is dependent upon a capacitance, or converting a variable capacitance output, of a sensor capacitor for example, into a digital format. By activating and deactivating pins, a microprocessor may form various circuits, for instance, each containing a resistor and a different capacitor and, in some embodiments, without the use of intermediate switching components. The microprocessor may alternately measure the time to change the charge of each of the capacitors and then calculate the capacitance of one of the capacitors using the measured times and known capacitances of one or more reference capacitors. Certain embodiments use two reference capacitors and alternately charge and discharge the capacitors, and a simple formula may be used to calculate capacitance using times to reach a threshold voltage. A measured parameter may be humidity or pressure, for example.

34 Claims, 3 Drawing Sheets

U.S. PATENT DOCUMENTS

| | | | |
|---|---|---|---|
| 6,353,324 B1 * | 3/2002 | Uber et al. ................ | 324/457 |
| 6,647,782 B2 | 11/2003 | Toyoda | |
| 6,661,239 B1 | 12/2003 | Ozick | |
| 6,710,629 B2 * | 3/2004 | Lee .......................... | 327/58 |
| 6,724,612 B2 | 4/2004 | Davis et al. | |
| 6,867,602 B2 | 3/2005 | Davis et al. | |
| 2004/0032268 A1 | 2/2004 | Schulte | |
| 2004/0051396 A1 | 3/2004 | Supper et al. | |
| 2004/0190327 A1 | 9/2004 | Baker | |

* cited by examiner

SENSOR OR CAPACITANCE MEASURING WITH A MICROPROCESSOR

CROSS-REFERENCE TO RELATED APPLICATION

This application claims priority to, and the benefit of, U.S. Provisional Application Ser. No. 60/583,159 filed Jun. 25, 2004, and entitled "Sensor Interface Circuit", which is hereby incorporated by reference.

FIELD OF INVENTION

This invention generally relates to systems and methods for measuring capacitance and may be used, for example, with a sensor capacitor to measure a parameter such as relative humidity or pressure. This invention also relates to systems and methods for producing a digital output from a capacitor, such as a sensor capacitor, or converting the output of a capacitor into a digital format.

BACKGROUND OF THE INVENTION

Systems and methods have been developed to measure capacitance, and various sensor capacitors have been used to detect or measure a number of parameters including relative humidity and pressure. Many such systems and methods have been complex, have required precise voltages for accuracy, or both, and therefore were costly. Microprocessors have been used to measure capacitance, but external components, such as intermediate switching components were required in many designs, which increased complexity and cost. Reference capacitors have been used in conjunction with sensor capacitors, but in many applications, only one reference capacitor was used. Such applications using a single reference capacitor eliminated some sources of error, but other sources of error were not eliminated. In other applications, complex calculations, such as Fourier transforms were required to determine capacitance, which required more complex or costly microprocessors. Some earlier systems and methods required precise voltages, precise currents, precise comparators, or a combination thereof, which added to cost and complexity, decreased accuracy, or both.

Therefore, a need exists for systems, devices, and methods for measuring capacitance, measuring various parameters using sensor capacitors, providing digital outputs, or a combination thereof, that are less complex, less costly, require fewer components, are more accurate, or a combination of such benefits. Potential for improvement exists in these and other areas that may be apparent to a person of skill in the art having studied this document.

SUMMARY OF PARTICULAR EMBODIMENTS OF THE INVENTION

Embodiments of this invention include methods, systems, and devices or apparatuses for measuring parameters, such as humidity, determining or measuring capacitance, such as capacitance of a sensor capacitor, producing a digital output that is dependent upon a capacitance, such as that of a sensor capacitor, or converting a variable capacitance output, of a sensor capacitor for example, into a digital format.

Various embodiments of the invention provide as an object or benefit that they partially or fully address one or more of the needs or potential for improvement described herein, for instance, in the background section above. The present invention provides various embodiments that may be less complex, less costly, more accurate, more reliable, or a combination thereof, in comparison with various prior art. Further features and advantages of the invention may be apparent to those skilled in the art.

In a specific embodiment, this invention provides an apparatus for measuring a parameter. The apparatus may include a microprocessor having a plurality of pins and a sensor capacitor configured to change capacitance as the parameter changes. The sensor capacitor may have a first lead electrically connected to a first pin of the microprocessor, and a second lead electrically connected to a second pin of the microprocessor. The apparatus may further include a first reference capacitor which may have a first lead electrically connected to a third pin of the microprocessor, and a second lead electrically connected to the second pin of the microprocessor mentioned above. The apparatus may further include a resistor which may have a first lead electrically connected to a fourth pin of the microprocessor, and a second lead electrically connected to the second pin of the microprocessor. In some embodiments, the apparatus may further include a second reference capacitor that may have a first lead electrically connected to a fifth pin of the microprocessor, and a second lead electrically connected to the second pin of the microprocessor.

In some embodiments of this apparatus, the parameter is a measure of the relative presence of a substance. In certain embodiments the parameter may be or include humidity, pressure, force, acceleration, proximity, or displacement, as examples. In particular embodiments, the apparatus may further include a voltage comparator, a timer, or both. The apparatus may be configured to use the timer to measure how long it takes for the sensor capacitor to reach the threshold voltage, how long it takes for the first reference capacitor to reach the threshold voltage, and in some embodiments, how long it takes for the second reference capacitor to reach the threshold voltage.

In certain embodiments of the invention, the sensor capacitance may be calculated using the formula: Sensor Capacitance=[(TimerS−Timer1)/(Timer2−Timer1)](Ref2−Ref1)+Ref1, where TimerS is the time for the sensor capacitor to reach the threshold voltage, Timer1 is the time for the first reference capacitor to reach the threshold voltage, Timer2 is the time for the second reference capacitor to reach the threshold voltage, Ref1 is the capacitance of the first reference capacitor, and Ref2 is the capacitance of the second reference capacitor. A number of embodiments further include software configured to control the microprocessor so that at least the first pin, the third pin, and the fifth pin are alternately activated, and when not activated, are left in a high-impedance state. In certain embodiments, such software may be configured so that when activated, these pins are driven as outputs to one of a first voltage and a second voltage. In select embodiments, the software may be configured so that the second pin is alternately activated as an output and as an input to a comparator, and when activated as an output, is driven to one of the first voltage and the second voltage.

In another specific embodiment, this invention provides a method of measuring the capacitance of a first capacitor. The method may include a number of steps that may be performed in any order except where order is indicated. These steps may include activating at least a first pin of a microprocessor that is electrically connected to the first capacitor, and while the first pin is activated, measuring a time to change the charge of the first capacitor. After measuring the time to change the charge of the first capacitor, the method may include the steps of deactivating the first pin into a high impedance state, and activating at least a second pin of a microprocessor that is electrically connected to a second capacitor. The method may then include, while the second pin is activated, measuring a time to change the charge of the second capacitor. And after measuring the time to change the charge of the second capacitor, the method may also include deactivating the second pin into a high impedance state, and activating at least a third pin of the microprocessor, that is electrically connected to a third capacitor. The method may further include, while the third pin is activated, the step of measuring a time to change the charge of the third capacitor. Further, after measuring the time to change the charge of the third capacitor, the method may include deactivating the third pin into a high impedance state. Still further, the method may include using at least the time to change the charge of the first capacitor, the time to change the charge of the second capacitor, and the time to change the charge of the third capacitor, to calculate the capacitance of the first capacitor.

In various embodiments of such a method, the second capacitor and third capacitor are reference capacitors that may have known capacitances, and the step of calculating the capacitance of the first capacitor includes finding the difference in capacitance between the second capacitor and the third capacitor. In addition, in various embodiments, the step of calculating the capacitance of the first capacitor includes adding the capacitance of the second capacitor, finding the difference between the time to change the charge of the first capacitor and the time to change the charge of the second capacitor, finding the difference between the time to change the charge of the second capacitor and the time to change the charge of the third capacitor, or a combination thereof. In various embodiments, the step of calculating the capacitance of the first capacitor may be undertaken using the formula described above: Furthermore, several embodiments include detecting when a threshold voltage is reached and measuring the time to reach the threshold voltage. Further, for some embodiments of the invention, the steps of measuring a time to change the charge of the second capacitor, and the step of measuring a time to change the charge of the third capacitor are repeated, in any order, alternating between charging and discharging the first, second, and third capacitors.

Yet another specific embodiment of the invention provides an apparatus for determining the capacitance of a sensor capacitor. This apparatus may include a first reference capacitor, a voltage comparator, a timer, and a microprocessor that may include a first pin electrically connected to the sensor capacitor and a second pin electrically connected to the first reference capacitor. The microprocessor may be configured to activate the first pin, the second pin, or both as an output and drive the pin(s) to a first voltage or to a second voltage, and to deactivate the pin(s) into a high-impedance state. The microprocessor may also have at least one third pin electrically connected to at least one of the sensor capacitor and the first reference capacitor, and the microprocessor may be configured to activate at least one third pin as an output and drive the at least one third pin to the first voltage or to the second voltage, and the microprocessor may further be configured to activate at least one third pin as an input to the comparator and to use the timer to measure the time for the sensor capacitor and the first reference capacitor to change from the first voltage to a first threshold voltage. The first threshold voltage may be between the first voltage and the second voltage, for example. In some embodiments, the microprocessor may further be configured to use at least these time measurements, and the capacitance of the first reference capacitor to calculate the capacitance of the sensor capacitor.

Certain embodiments of this apparatus may further include a second reference capacitor, and the microprocessor may have a fourth pin electrically connected to the second reference capacitor. In such embodiments, the microprocessor may be configured to activate the fourth pin as an output and drive the fourth pin to the first or second voltage, or to deactivate the fourth pin into a high-impedance state. Further, the microprocessor may be configured to use the timer to measure the time for the second reference capacitor to change from the first voltage to the first threshold voltage, and the microprocessor may be configured to use at least the times that were measured and the capacitances of the first and second reference capacitors to calculate the capacitance of the sensor capacitor. Still further, in certain embodiments, the microprocessor may be configured to use the timer to measure the time for the sensor capacitor to change from the second voltage to a second threshold voltage, to use the timer to measure the time for the first reference capacitor to change from the second voltage to the second threshold voltage, and to use these times and the capacitance of the reference capacitor(s) to calculate the capacitance of the sensor capacitor. Various embodiments may further include a resistor, and a fifth pin may be electrically connected to the resistor. In such embodiments, the microprocessor may be configured to drive the fifth pin to the first voltage or to the second voltage, and may be configured to pass electrical current through the resistor when measuring the various lengths of time.

Still another specific embodiment of the invention provides an apparatus for producing a digital output that is dependent upon a capacitance of a sensor capacitor. This apparatus may include a microprocessor with a plurality of pins, and a sensor capacitor with a first lead electrically connected to a first pin of the microprocessor and a second lead electrically connected to at least one common pin of the microprocessor. The apparatus may further include a first reference capacitor with a first lead electrically connected to a second pin of the microprocessor, and a second lead electrically connected to at least one common pin of the microprocessor. The apparatus may further include a resistor with a first lead electrically connected to a third pin of the microprocessor and a second lead electrically connected to at least one common pin of the microprocessor. The microprocessor may be configured to activate the first pin and at least one common pin as voltage outputs to apply a first voltage across the sensor capacitor, activate the third pin as a voltage output to establish a first current through the resistor, deactivate at least one common pin as a voltage output, activate at least one common pin as a comparator input, measure the time for a voltage across the sensor capacitor to reach a threshold voltage using the comparator input, and deactivate the first pin to a high-impedance state.

In such an apparatus the microprocessor may further be configured to activate the second pin and at least one common pin as voltage outputs to apply the first voltage across the first reference capacitor, activate the third pin as a voltage output to establish the first current through the resistor, deactivate at least one common pin as a voltage output, activate at least one common pin as a comparator input, measure the time for the voltage across the first reference capacitor to reach the threshold voltage using the comparator input, and deactivate the second pin to a high-impedance state. The microprocessor may be still further configured to calculate a digital output that is dependent upon the capacitance of the sensor capacitor using at least the time for the voltage across the sensor capacitor to reach the threshold voltage and the time for the voltage across the first reference capacitor to reach the threshold voltage.

Certain embodiments of this apparatus may further include a second reference capacitor that may have a first lead electrically connected to a fourth pin of the microprocessor and a second lead electrically connected to at least one common pin of the microprocessor, and the microprocessor may be further configured to activate the fourth pin and at least one common pin as voltage outputs to apply the first voltage across the second reference capacitor, activate the third pin as a voltage output to establish a first current through the resistor, deactivate at least one common pin as a voltage output, activate at least one common pin as a comparator input, measure the time for the voltage across the second reference capacitor to reach the threshold voltage using the comparator input, and deactivate the fourth pin to a high-impedance state. In such an embodiment, the microprocessor may be further configured to calculate the digital output that is dependent upon the capacitance of the sensor capacitor using at least the time for the voltage across the sensor capacitor to reach the threshold voltage, the time for the voltage across the first reference capacitor to reach the threshold voltage, and the time for the voltage across the second reference capacitor to reach the threshold voltage.

Even another specific embodiment of the invention provides a method of converting the variable capacitance output of a sensor capacitor into a digital format. This method may include various steps that may be performed in any order using a microprocessor without the use of intermediate switching components. These steps may include forming a circuit to facilitate changing the charge of the sensor capacitor, and changing the charge of the sensor capacitor while measuring the time required to do so. The method may also include reconfiguring the circuit to facilitate changing the charge of a first reference capacitor, and changing the charge of the first reference capacitor while measuring the time required. This method may also include the step of reconfiguring the circuit to facilitate changing the charge of a second reference capacitor, and changing the charge of the second reference capacitor while measuring the time required to do so. This method may further include using at least the time required to change the charge of the sensor capacitor, the time required to change the charge of the first reference capacitor, and the time required to change the charge of the second reference capacitor, calculating a digital output that is dependent upon the capacitance of the sensor capacitor.

In various embodiments of this method, the steps of changing the charge of the sensor capacitor, changing the charge of the first reference capacitor, and changing the charge of the second reference capacitor may be accomplished by passing current through a common resistor electrically connected to the microprocessor without any intermediate switching components there between. In particular embodiments, the steps of changing the charge of the sensor capacitor, changing the charge of the first reference capacitor, and changing the charge of the second reference capacitor may all be accomplished by changing the charge from a common first voltage to a common threshold voltage. In certain embodiments, the changing of the charge of the sensor capacitor and the changing of the charge of the first reference capacitor are repeated, alternating between changing from a lower potential to a higher potential, and changing from a higher potential to a lower potential. Further, in a range of embodiments, the step of calculating a digital output may involve using the formula described above.

BRIEF DESCRIPTION OF THE DRAWINGS

The figures in this document illustrate various exemplary embodiments of the present invention, wherein like reference numerals represent like elements. Embodiments of the invention may include part or all of the features shown in one of these drawings, or may include features from two or more figures. Accordingly.

DETAILED DESCRIPTION OF EXAMPLES OF EMBODIMENTS

Various embodiments of the invention include systems, apparatuses, and methods for measuring capacitance, which may be used, for example, with a sensor capacitor to measure a parameter such as relative humidity. Certain embodiments include systems, devices, and methods for producing a digital output from a capacitor, such as a sensor capacitor, or converting the output of a capacitor into a digital format. Many embodiments use a microprocessor to dynamically configure various charge/discharge circuits from a limited set of components, in many embodiments, without the use of any other intermediate components. Components that are used in various embodiments include a resistor, a sensor capacitor, a first reference capacitor, and in some embodiments, a second reference capacitor. Circuits may be formed that contain a resistor and a capacitor (i.e., an RC circuit). In a number of embodiments, different RC circuits may be configured alternately using different capacitors, and in some embodiments, the reconfiguration of the circuitry may be performed by a microprocessor without the use of external or intermediate switching components.

In embodiments that have two reference capacitors, the use of two such reference capacitors may cancel errors due to offset voltages, currents, noise, and the like. Some embodiments of the invention allow the reference capacitor or capacitors and the sensor capacitor to be alternately charged and discharged using only 1 microprocessor pin per reference component or sensor plus one common pin. Certain embodiments also provide a signal calculation system or method which reduces the potentially complex use of two reference capacitors to a calculation which, in some embodiments, can be carried out using a relatively simple, low-cost microprocessor.

A number of embodiments of the invention use a fixed cycle driven by the microprocessor to alternately charge and discharge the various capacitors. In many embodiments, total measurement time for the one or two reference capacitors and the sensor capacitor may be less than the time that typically would be required for there to be a measurable change in ambient conditions. Thus, the ambient conditions may be unchanged, for all practical purposes, while a particular set of measurements is taken. In some embodiments, errors that are either constant or can be approximated by a linear function of the sensor capacitance can be corrected or cancelled using the system or method described herein.

Figure 1:
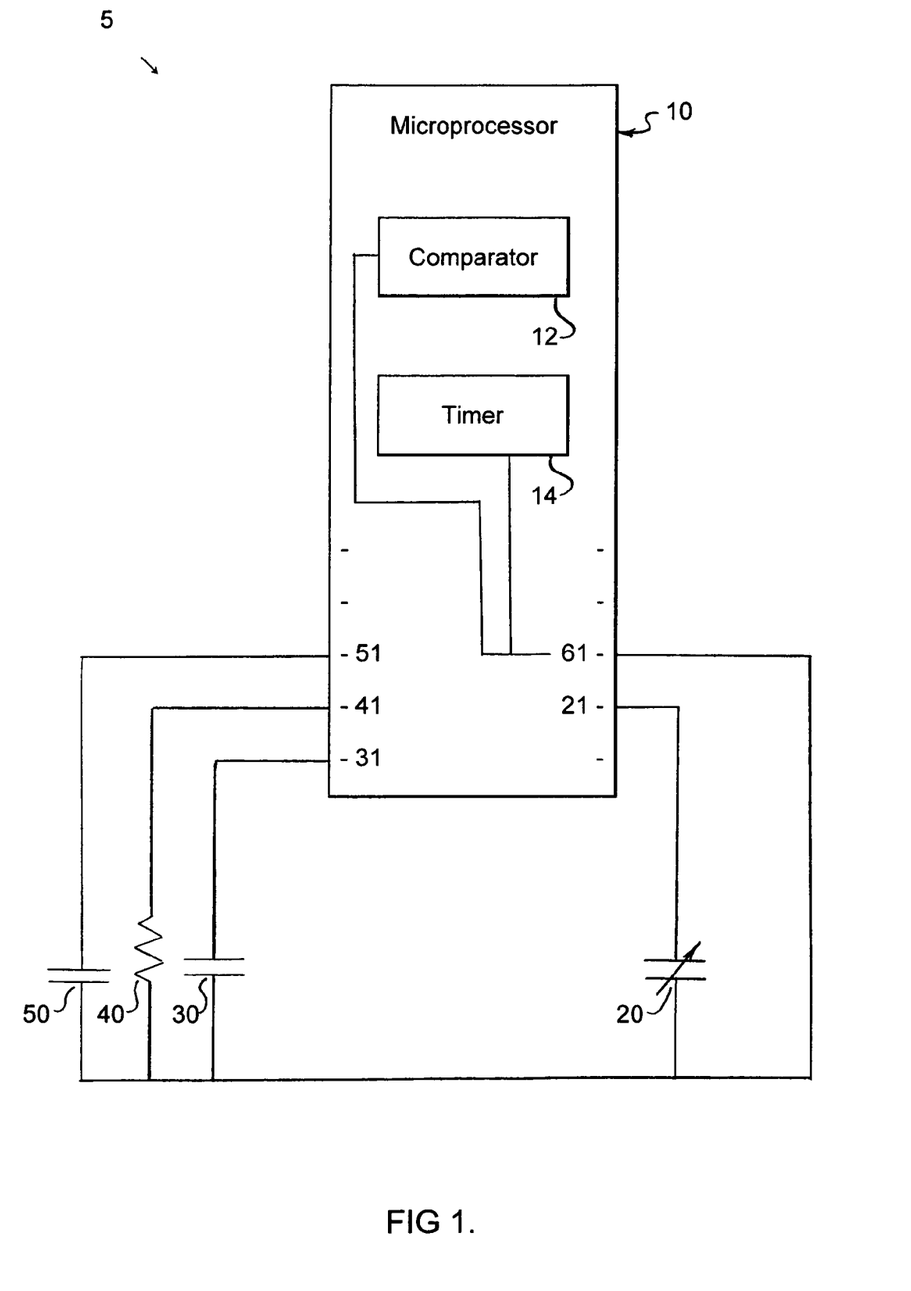
FIG. 1 is an electrical schematic illustrating an exemplary embodiment of an apparatus or system in accordance with the invention.

An example of an embodiment of a system or apparatus 5 in accordance with this invention is illustrated in FIG. 1. Apparatus 5 may include a processor or microprocessor 10, which may have a plurality of pins, such as pins 21, 31, 41, 51, and 61 described herein, and may have other pins used for other functions. Microprocessor 10 may be a chip and may be of a type that is capable of driving certain pins to at least one voltage and also capable of deactivating those pins to a high-impedance state. In some embodiments, microprocessor 10 may be able to drive pins to one of at least two voltages. In a specific embodiment, microprocessor 10 may be a PIC16F630 microprocessor. Microprocessor 10 would generally be powered by a power supply, which in certain embodiments, may be a battery.

Certain embodiments of apparatus 5 may include comparator 12, timer 14, or both, which in some embodiments, may be part of microprocessor 10. In some embodiments, microprocessor 10 may be able to deactivate at least one pin as an output, and enable that pin as an input, for example, to comparator 12. Comparator 12 may be configured to detect or measure at least one threshold voltage. In some embodiments, comparator 12 may be configured to detect or measure two different threshold voltages, or more, which may be, for example, between the first voltage and the second voltage described herein. Timer 14 may be configured to measure time. In some embodiments, timer 14 and comparator 12 may be used together to measure, for example, a length of time until a particular voltage is reached. In certain embodiments, apparatus 5 may be configured to use timer 14, comparator 12, or both, to measure how long it takes to reach a threshold voltage. Further, in some embodiments, apparatus 5 may include sensor capacitor 20, resistor 40, and one, two, or more reference capacitors, for example, reference capacitors 30 and 50 shown. In particular embodiments, apparatus 5 may be configured to use timer 14, comparator 12, or both, to measure how long it takes for each of sensor capacitor 20, reference capacitor 30, reference capacitor 50, or a combination thereof, to reach a threshold voltage. In one embodiment, resistor 40 has a resistance of 1.6 megohms.

In various embodiments, reference capacitors 30, 50, or both, may have stable or known capacitances. The capacitance of reference capacitors 30, 50, or both, may remain relatively constant and not change, for example, as the parameter measured by sensor capacitor 20 changes. In other embodiments, the capacitance of reference capacitors (e.g., 30, 50, or both) may change as a parameter changes, but the parameter may be known or controllable, for example, where the reference capacitor is located.

In certain embodiments that have two reference capacitors 30 and 50, the capacitance of reference capacitor 30 and reference capacitor 50 may differ. In some embodiments, sensor capacitor 20 may have a capacitance that varies over a range, for example, as the parameter being measured varies. The capacitance of first reference capacitor 30 may be at or near one end of this range, while the capacitance of reference capacitor 50 may be at or near the other end of this range. For instance, The capacitance of first reference capacitor 30 may be close to or approximately equal to the minimum capacitance of sensor capacitor 20 and the capacitance of reference capacitor 50 may be close to or approximately equal to the maximum capacitance of sensor capacitor 20.

In certain embodiments, it may be more important that the capacitances of capacitors 30 and 50 be stable, than it is important that these capacitances have a particular value, provided the capacitances of capacitors 30 and 50 are not the same. In particular embodiments, reference capacitor 30 has a capacitance of about 150 picofarads, and reference capacitor 50 has a capacitance of about 200 picofarads. In some embodiments, the capacitances of capacitors 30 and 50 are known, and in certain embodiments, one or both of these capacitances may be precisely known. But in different embodiments, the precise capacitance values of capacitors 30 and 50, for example, may not be known. In particular embodiments, rather than knowing the precise capacitance values of capacitors 30 and 50, the apparatus may be calibrated, for instance, based on one or more measurements taken at a time and location when and where the parameter being measured is known, or when the capacitance of capacitor 20, for example, is known.

System or apparatus 5 may include various electrical connections, conductors, wires, and the like, for example, as illustrated. In some embodiments, one or more of capacitors 20, 30, and 50 and resistor 40 may be located remotely from microprocessor 10. In some embodiments, there may be more than one sensor capacitor 20, which may have common or different reference capacitor(s) (e.g., 30 and 50) microprocessor 10, resistor 40, conductors, and the like. In some embodiments more than one sensor capacitor 20 may be located in different locations to measure the same parameter at different locations. In some embodiments, more than one sensor capacitor 20 may be located at the same location to measure different parameters at the same location or to provide redundancy for improved accuracy or reliability, for example. In some such embodiments, more than one sensor capacitor may be used with one microprocessor 10. Yet in other embodiments, the components illustrated in FIG. 1 may be provided as a unit for use with a single sensor capacitor 20.

Sensor capacitor 20 may be configured to change capacitance as a particular parameter changes. Thus, sensor capacitor may be configured to measure that parameter. For instance, the capacitance of sensor capacitor 20 may change when the relative presence of a substance changes. In other words, the parameter that sensor capacitor measures may be a measure of the relative presence of a substance. One example of such a substance, is water or humidity. In such embodiments, sensor capacitor 20 may be configured to measure humidity, or, for example, relative humidity. In particular embodiments, sensor capacitor 20 is item HS1101 by Humirel. In other embodiments, sensor capacitor 20 may be configured to measure pressure or temperature, for example. In other embodiments, sensor capacitor 20 may measure a force, for example, in an electronic scale, or may measure acceleration, for example, to detect or quantify vibration. In another embodiment, capacitor may be a proximity sensor, and may detect the presence or distance away of a material through capacitance change, or may be a distance sensor, sensing the distance between capacitor plates, one of which is mechanically connected to the object who's distance is being measured.

In some embodiments of the invention, a capacitor may be used in place of sensor capacitor 20 that may not be used as a sensor capacitor, but the capacitance of which may be desired. In such embodiments, the capacitance may not change relative to a particular parameter of interest.

As illustrated, in certain embodiments, various components of system or apparatus 5 may have leads that may be electrically connected to various pins of microprocessor 10. As illustrated, in many embodiments such connections may be formed without the use of intermediate switching components. In other words, in such embodiments, no switching components are provided between pins 21, 31, and 51 of microprocessor 10 and capacitors 20, 30, and 50, or between pin 41 and resistor 40, or between capacitors 20, 30, and 50 and resistor 40 and pin 61, or a combination thereof. Intermediate switching components, as used herein, may include multiplexers, transistors, relays, or the like, for example, between pins 21, 31, and 51 of microprocessor 10 and capacitors 20, 30, and 50, or between pin 41 and resistor 40, or between capacitors 20, 30, and 50 and resistor 40 and pin 61, or a combination thereof. Various components, such as sensor capacitor 20, reference capacitors 30, 50, or both, resistor 40, or a combination thereof, may have two leads, which may be referred to herein as a first lead and a second lead, that may both be electrically connected to different pins of microprocessor 10, for example, as shown in FIG. 1.

In various embodiments pins 21, 31, 41, and 51 of microprocessor 10 may serve or function as outputs. In such embodiments, pins 21, 31, 41, and 51 may output (from microprocessor 10) at least one voltage. In other words, microprocessor 10 may be configured to drive these pins to at least one voltage. In some embodiments, microprocessor 10 may be configured to selectively or alternately drive pins 21, 31, 41, and 51 to one of two voltages, for example, a first voltage and a second voltage. In particular embodiments, one of the first voltage and the second voltage may be a ground, zero volts, or near zero volts, and the other of the first voltage and the second voltage may be a non-zero voltage, for example, the power voltage supplied to microprocessor 10, which may be, for example, about five (5) volts.

In many embodiments of the invention, microprocessor 10 may be configured to deactivate some or all of pins 21, 31, 41, and 51 into a high impedance state. As used herein, when deactivated, a pin does not provide an output voltage and is not driven to a particular voltage by microprocessor 10. Thus, the voltage at a deactivated pin may float or be determined in accordance with activities in the circuit external to microprocessor 10. By deactivating certain pins, microprocessor may take various components out of the circuit and may form or configure various circuits with the components that are electrically connected to pins that are activated.

In some embodiments, microprocessor 10 may not deactivate some pins into a high impedance state, for example, pin 41 connected to resistor 40. In fact, some embodiments may omit pin 41 connected to resistor 40, and the lead of resistor 40 that is shown connected to pin 41 may be connected to a ground or voltage source, the first voltage or the second voltage described above, or the like. In other embodiments, resistor 40 may be connected to pin 41, but pin 41 may only be activated at the first voltage or the second voltage. In some embodiments, microprocessor 10 may be configured to drive pin 41 to the first voltage, and microprocessor 10 may be configured to drive pin 41 to second voltage. But in such embodiments microprocessor 10 may or may not be configured to deactivate pin 41 to a high-impedance state. In some embodiments, pins 21, 31, 41, 51, or a combination thereof, may be configured to serve only as outputs (when activated) and may not be configured to serve as inputs at all.

In the embodiment illustrated, capacitors 20, 30, and 50 and resistor 40 are all connected to a common pin 61. In some embodiments, pin 61 may serve as an output. Thus, microprocessor 10 may be configured to drive pin 61 to at least one voltage. In some embodiments, microprocessor 10 may be configured to selectively or alternately drive pin 61 to more than one voltage, for example, a first voltage and a second voltage, such as described above for pins 21, 31, 41, and 51, for example. In some embodiments, microprocessor may also be configured to activate pin 61 as an input. In such an embodiment, pin 61 may be an input to comparator 12, for example. In some embodiments, while serving as an input, pin 61 may be deactivated as an output, and may be in a high-impedance state, such that microprocessor 10 does not drive the voltage of pin 61. In some embodiments, pin 61 may be activated as an input to comparator 12 at all times or for periods of time, for example, while a number of voltage measurements are taken. As used herein, activating a pin as an input includes maintaining a pin activated as an input.

In the embodiment illustrated, where capacitors 20, 30, and 50 and resistor 40 are all connected to a common pin 61, a relatively low number of pins (five (5) pins) of microprocessor 10 are used for these four components. Embodiments that use only one reference capacitor may use only four pins. Embodiments for which resistor 40 is not connected to a pin may use one fewer pins of microprocessor 10. However, in other embodiments of the invention, capacitors 20, 30, and 50 resistor 40, or a combination thereof, may be connected (at the lead that is shown in FIG. 1 as being connected to pin 61) to more than one pin, which may be referred to herein as common pins (or at least one common pin, if such an embodiment is included). Such embodiments include, as examples, an embodiment wherein capacitors 20, 30, and 50 and resistor 40 are connected (at the lead that is shown in FIG. 1 as being connected to pin 61) to two pins, one of which may function as an output and one of which may function as an input, for example, to comparator 12. In another embodiment with common pins, each of capacitors 20, 30, and 50 and resistor 40 may be connected (at the lead that is shown in FIG. 1 as being connected to pin 61) to its own pin, which may be connected through microprocessor 10 to form various circuits which may be analogous to those described herein, for example. Other configurations of more than one common pin in lieu of common pin 61 would be apparent to a skilled circuit designer.

The invention may further include or utilize software that may be loaded onto microprocessor 10 and may control microprocessor 10. Such software may configure microprocessor 10 to take steps or perform functions described herein. This software may be configured to control microprocessor 10, for example, so that various pins are alternately activated and deactivated, times to reach a threshold voltage are measured, and the like. In a particular embodiment, this software may be written as source code, for example, in C, and then compiled into machine language or object code and loaded onto non-volatile memory of microprocessor 10 or an external memory, which may also be non-volatile.

Figure 2:
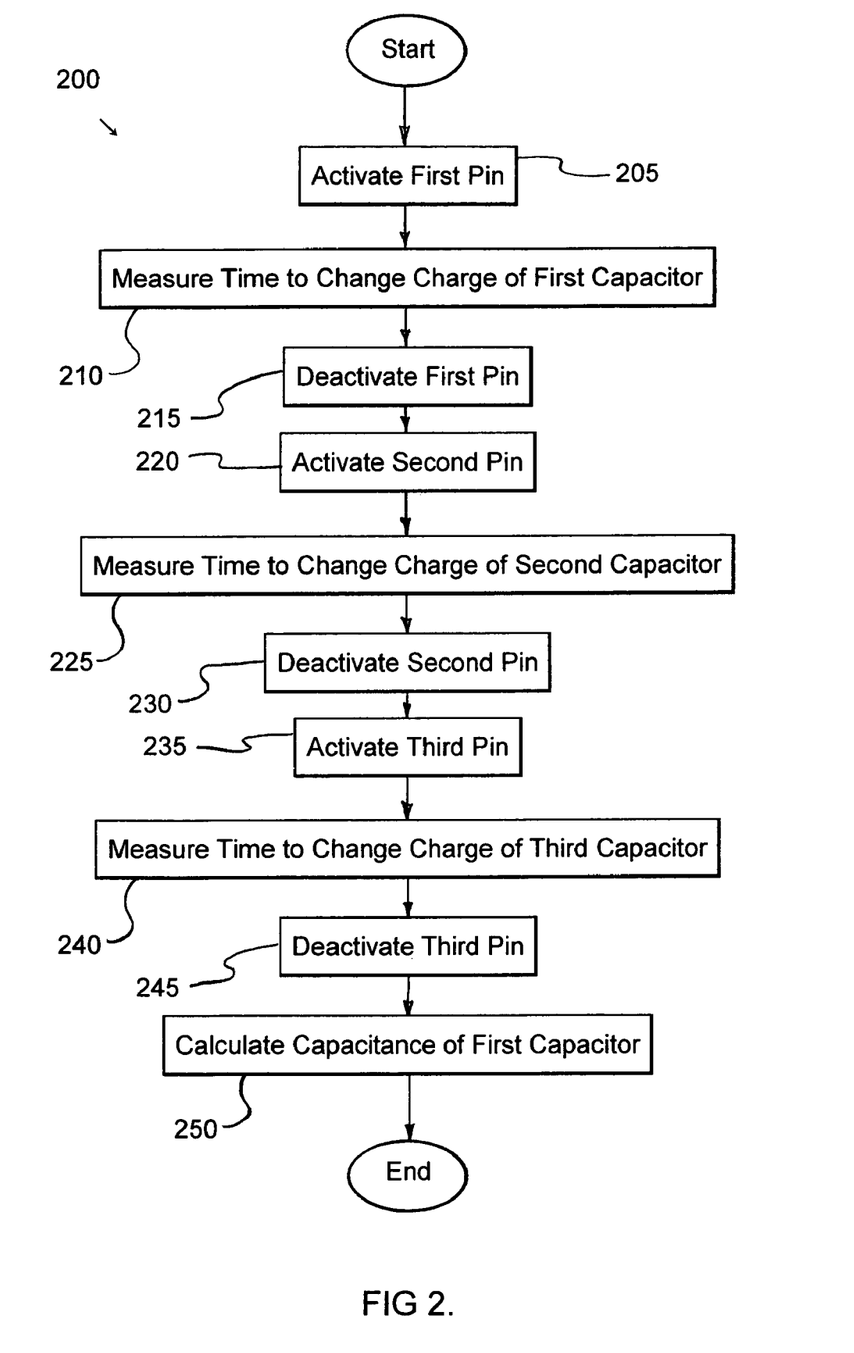
FIG. 2 is a flow chart illustrating various steps that may be completed in an exemplary method in accordance with the invention.

FIG. 2 illustrates an example of a method in accordance with the invention, method 200, which may be carried out, for example, using apparatus 5 shown in FIG. 1. Method 200 includes the step of activating a first pin (step 205), for example, pin 21 of microprocessor 10, which may be electrically connected to a first capacitor, such as sensor capacitor 20, for example, as shown in FIG. 1. The first pin may be activated (step 205) as an output, for example, and may be driven to a first voltage or a second voltage, for instance, as described herein. In some embodiments, microprocessor 10 may be configured to activate the first pin (step 205) and drive the first pin alternately to a first voltage and a second voltage. Step 205 is an example of a method or step, or part of a method or step, of forming or reconfiguring a circuit to facilitate changing the charge of the first capacitor, for example, sensor capacitor 20, which may be accomplished without the use of intermediate switching components.

Method 200 may also include the step of measuring the time to change the charge of the first capacitor (step 210), which may be accomplished, in some embodiments, while the first pin is activated. In certain embodiments, the charge of the first capacitor may be changed while measuring the time required to change the charge. In some embodiments, the charge of the first capacitor may be changed from a first voltage or a second voltage to a threshold voltage. The threshold voltage may be between the first voltage and the second voltage, for example. In some embodiments, measuring the time to change the charge (step 210) may include detecting when a threshold voltage is reached, and measuring the time to reach the threshold voltage. In certain embodiments, the charge of the first capacitor, for example, sensor capacitor 20, may be changed, the time measured, or both, without the use of intermediate switching components.

Method 200 further includes the step of deactivating the first pin (step 215), for example, to a high-impedance state, which may be accomplished after the step of measuring the time to change the charge of the first capacitor (step 210).

These steps (steps 205, 210, and 215) may be repeated for a second pin and a second capacitor (steps 220, 225, and 230), a third pin and a third capacitor (steps 235, 240, and 245), or both, after which a result such as the capacitance of one of the capacitors may be calculated (step 250). In different embodiments, the time to charge the first and second or first, second, and third capacitors may be measured (for example, steps 210, 225, and 240) in different orders. In certain embodiments, the first second and third capacitors may correspond to sensor capacitor 20, first reference capacitor 30, and second reference capacitor 50, illustrated in FIG. 1, for example.

In some embodiments, the steps of changing the charge of capacitors (for example, as measured in steps 210, 225, and 240, e.g., capacitors 20, 30, and 50) may be accomplished by passing current through a common resistor (e.g., resistor 40) electrically connected to microprocessor 10, in certain embodiments, without any intermediate switching components there between. In a number of embodiments, the steps of changing the charge of these capacitors may be accomplished by changing the charge from a common first voltage to a common threshold voltage. In certain embodiments, use of the same common resistor, first voltage, threshold voltage, or a combination thereof, may result in more accurate results when measuring the time to charge the capacitors (steps 210, 225, and 240) or calculating capacitance (e.g., in step 250).

In the specific embodiment illustrated in FIG. 2, the second pin may be activated (step 220) as an output, for example, and may be driven to a first voltage or a second voltage, for instance, as described herein. In some embodiments, microprocessor 10 may be configured to activate the second pin (step 220) and drive the second pin alternately to a first voltage and a second voltage. Steps 215 and 220 are an example of a method or step, or part of a method or step, of forming or reconfiguring a circuit to facilitate changing the charge of the second capacitor, for example, first reference capacitor 30, which, in certain embodiments, may be accomplished without the use of intermediate switching components.

Method 200 may also include the step of measuring the time to change the charge of the second capacitor (step 225), which may be accomplished, in some embodiments, while the second pin is activated. In certain embodiments, the charge of the second capacitor may be changed while measuring the time required to change the charge. In some embodiments, the charge of the second capacitor may be changed from a first voltage or a second voltage to a threshold voltage. The threshold voltage may be between the first voltage and the second voltage, for example. In some embodiments, measuring the time to change the charge (step 225) may include detecting when a threshold voltage is reached, and measuring the time to reach the threshold voltage. Method 220 further includes the step of deactivating the second pin (step 230), for example, to a high-impedance state, which may be accomplished after the step of measuring the time to change the charge of the second capacitor (step 225). In certain embodiments, the charge of the second capacitor, for example, reference capacitor 30, may be changed, the time measured, or both, without the use of intermediate switching components.

Similarly, at least in embodiments that have two reference capacitors, and in the specific embodiment illustrated in FIG. 2, the third pin may be activated (step 235) as an output, for example, and may be driven to a first voltage or a second voltage, for instance, as described herein. In some embodiments, microprocessor 10 may be configured to activate the third pin (step 235) and drive the third pin alternately to a first voltage and a second voltage. Steps 230 and 235 are an example of a method or step, or part of a method or step, of forming or reconfiguring a circuit to facilitate changing the charge of the third capacitor, for example, second reference capacitor 50, which, in certain embodiments, may be accomplished without the use of intermediate switching components.

Method 200 may also include the step of measuring the time to change the charge of the third capacitor (step 240), which may be accomplished, in some embodiments, while the third pin is activated. In certain embodiments, the charge of the third capacitor may be changed while measuring the time required to change the charge. In some embodiments, the charge of the third capacitor may be changed from a first voltage or a second voltage to a threshold voltage. The threshold voltage may be between the first voltage and the second voltage, for example. In some embodiments, measuring the time to change the charge (step 240) may include detecting when a threshold voltage is reached, and measuring the time to reach the threshold voltage. In certain embodiments, the charge of the first capacitor, for example, reference capacitor 50, may be changed, the time measured, or both, without the use of intermediate switching components.

Method 235 further includes the step of deactivating the third pin (step 245), for example, to a high-impedance state, which may be accomplished after the step of measuring the time to change the charge of the third capacitor (step 240). Step 245 may be part of an example of a method or step, of reconfiguring a circuit to facilitate changing the charge of a capacitor, for example, sensor capacitor 20, which, in certain embodiments, may be accomplished without the use of intermediate switching components.

Method 200 may also include the step of calculating the capacitance of the first capacitor (step 250), which may be sensor capacitor 20 shown in FIG. 1. In some embodiments, the calculating the capacitance of the first capacitor (step 250) may be performed electronically, digitally, or both, for example, using microprocessor 10, and may be performed in real time or substantially in real time. In some embodiments, the step of calculating the capacitance of the first capacitor (step 250) may involve using or solving an equation or formula. Such a formula may require adding, subtracting, multiplying, dividing, or a combination thereof. But a number of embodiments of the invention do not require higher level mathematical operations. In many embodiments, the capacitance of the first capacitor may be calculated (step 250) without using iteration, without using Fourier transforms, without solving an infinite series, without exponential functions, without a combination of such operations, or without any such operations.

In particular embodiments, a digital output may be calculated that may be dependent upon the capacitance of the first capacitor, for instance, sensor capacitor 20. The capacitance of the first capacitor may be calculated (step 250), for example, using at least the time to change the charge of the first capacitor (for example, measured in step 210), the time to change the charge of the second capacitor (for example, measured in step 225), and (at least in embodiments that have a second reference capacitor) the time to change the charge of the third capacitor (for example, measured in step 240).

In certain embodiments, the second capacitor and the third capacitors may be reference capacitors which may have known capacitances. These capacitances may be different or unequal, and the step of calculating the capacitance of the first capacitor (step 250) may include finding the difference in capacitance between the second capacitor and the third capacitor. In some embodiments, microprocessor 10 may calculate this difference, while in other embodiments, this difference may have been previously calculated.

In a selection of embodiments, the step of calculating the capacitance of the first capacitor (step 250) may include adding the capacitance of one of the reference capacitances, for example, to another value. This reference capacitor may be the second capacitor or the third capacitor, for example. In other words, the step of calculating the capacitance of the first (sensor) capacitor (step 250) may include calculating the difference between the capacitance of one of the reference capacitors and the capacitance of the sensor capacitor, and adding that difference to the known capacitance of the reference capacitor to arrive at the capacitance of the sensor capacitor. As used herein, the word "adding" includes subtracting (which is equivalent to adding a negative number). In some embodiments, microprocessor 10 may perform this adding operation.

In certain embodiments, the step of calculating the capacitance of the first capacitor (step 250) may include finding the difference between the time to change the charge of the first capacitor and the time to change the charge of the second capacitor (for example, measured in steps 210 and 225 respectively), which may be, in some embodiments, sensor capacitor 20 and first reference capacitor 30, shown in FIG. 1. As used herein, "finding the difference" includes subtracting either value from the other value. In some embodiments, microprocessor 10 may perform this operation of finding the difference between the time to change the charge of the first capacitor and the time to change the charge of the second capacitor.

In a number of embodiments, for example, that include two reference capacitors (for instance, 30 and 50), the step of calculating the capacitance of the first capacitor (step 250) may include finding the difference between the time to change the charge of the second capacitor and the time to change the charge of the third capacitor (for example, measured in steps 225 and 240 respectively), which may be, in some embodiments, first reference capacitor 30 and second reference capacitor 50, shown in FIG. 1. In some embodiments, microprocessor 10 may perform this operation of finding the difference between the time to change the charge of the second capacitor and the time to change the charge of the third capacitor. In some embodiments, the step of finding the difference between the time to change the charge of the second capacitor and the time to change the charge of the third capacitor may be accomplished indirectly by finding the difference between the time to change the charge of the first capacitor and the time to change the charge of the third capacitor and adding the difference between the time to change the charge of the first capacitor and the time to change the charge of the second capacitor.

In an assortment of embodiments, the step of calculating the capacitance of the first capacitor (step 250) may include finding the difference between the time to change the charge of the first capacitor and the time to change the charge of the second capacitor, and dividing this quantity by the difference between the time to change the charge of the second capacitor and the time to change the charge of the third capacitor. In particular embodiments, this quantity may be divided by the difference in capacitance between the second capacitor and the third capacitor. In some embodiments, microprocessor 10 may perform one or more of these operations.

In particular embodiments, the step of calculating the capacitance of the first capacitor (step 250) may include using the formula:

$$\text{Sensor Capacitance} = [(\text{TimerS} - \text{Timer1})/(\text{Timer2} - \text{Timer1})](\text{Ref2} - \text{Ref1}) + \text{Ref1}$$

wherein:

TimerS is the time to change the charge of the first capacitor,

Timer1 is the time to change the charge of the second capacitor,

Timer2 is the time to change the charge of the third capacitor,

Ref1 is the capacitance of the second capacitor, and

Ref2 is the capacitance of the third capacitor.

In some embodiments, a digital output may be produced, displayed, or sent, which may be, for example, calculated in method 200 or step 250. In a number of embodiments, a digital output may be produced, for example, that is dependent upon a capacitance, for instance, of sensor capacitor 20. In particular embodiments, such a digital output may be converted to an analog output, while in other embodiments the output may remain in digital form. An output may be produced, for example, in the form of a relative humidity, absolute pressure, gauge pressure, temperature, force, acceleration, vibration amplitude, or distance, as examples, which may be displayed, logged, provided as an input to a controller, used to control equipment, used in a feedback control system, used to trigger an alarm, or the like.

Figure 3:
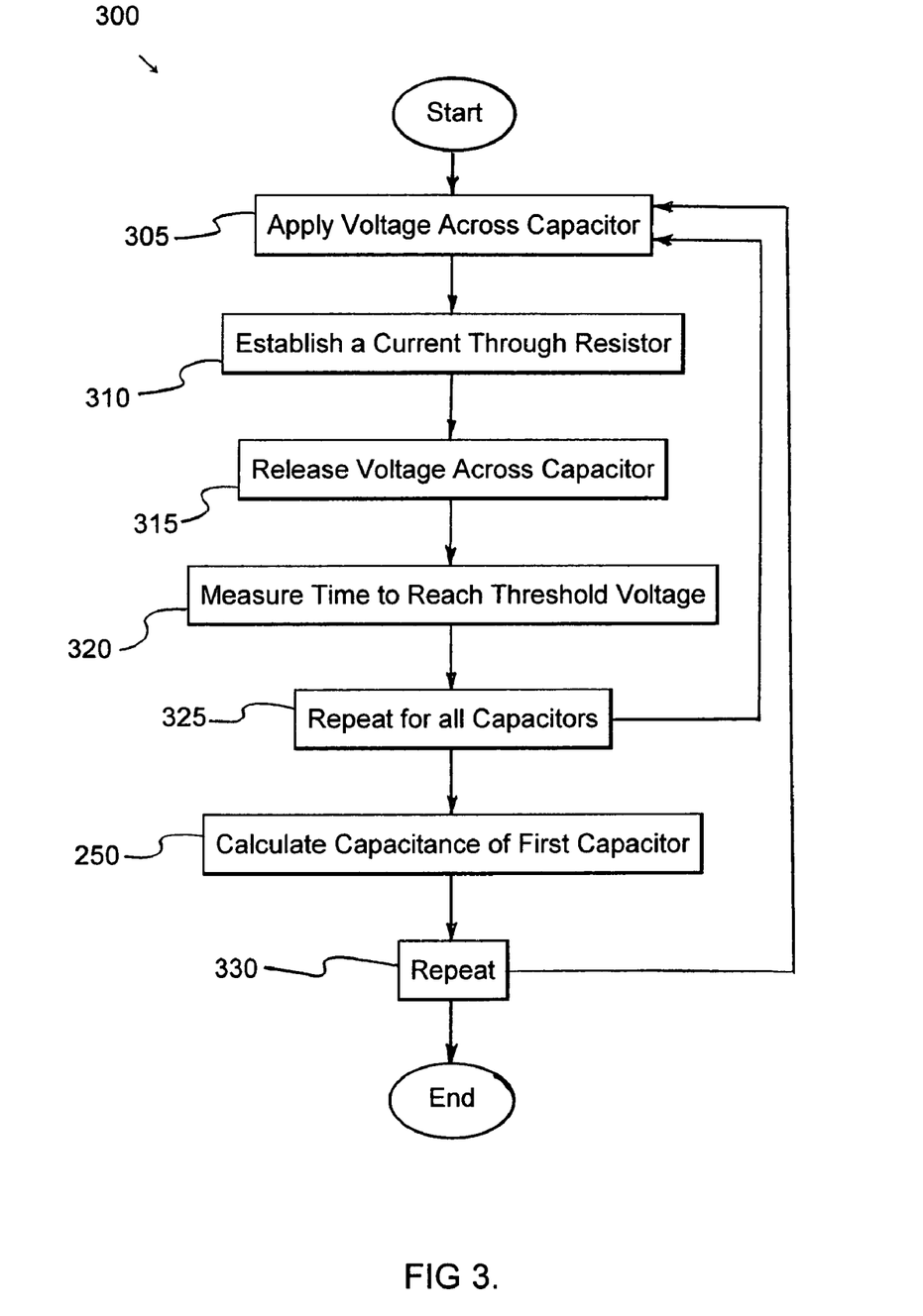
FIG. 3 is a flow chart illustrating various steps that may be completed in another exemplary method in accordance with the invention.

FIG. 3 illustrates method 300 in accordance with the invention, that depicts an example of a method of changing the charge of capacitors. For instance, in method 300, the charges of sensor capacitor 20, first reference capacitor 30, second reference capacitor 50, or a combination thereof, may be changed, for example, as per steps 210, 225, 240, or a combination thereof, in method 200. In different embodiments, the capacitors (e.g., 20, 30, 50, or a combination thereof) may be charged or discharged in various orders.

As illustrated, method 300 may include applying a voltage across a capacitor (step 305). This may be accomplished, for example, in the case of sensor capacitor 20, by activating pins 21 and 61 as voltage outputs, for instance, to the first voltage or the second voltage described herein. In this example, pins 21 and 61 may be driven to the same or different voltages. If pins 21 and 61 are driven to the same voltage (whether the first voltage or the second voltage), then sensor capacitor 20 would have a known charge across it of zero voltage, or would be completely discharged. On the other hand, if pins 21 and 61 are driven to different voltages, for example, the first voltage and the second voltage, then the voltage across sensor capacitor 20 would be the difference between the first voltage and the second voltage. In embodiments where the first voltage is zero volts, then the charge across capacitor 20 may be the second voltage for example.

Method 300 may also include the step of establishing a current through a resistor (step 310), which may be resistor 40, for example. In different embodiments, steps 305 and 310 may be accomplished in either order or at the same time. In this example, the current (of step 310) may be established by activating pins 41 and 61 as outputs (or keeping them activated if one or both were already activated as an output) and driving these pins to a particular voltage, for example, to the first voltage or the second voltage. In this example, pins 41 and 61 are driven to different voltages. If pins 41 and 61 are driven to the first voltage and the second voltage, then the voltage across resistor 40 would be the difference between the first voltage and the second voltage. In embodiments where the first voltage is zero volts, then the potential across resistor 40 would be the second voltage, and a corresponding non-zero current would be established (step 310) through resistor 40.

Thus, in various embodiments of method 300, after steps 305 and 310 are completed, pins 21, 41, and 61 are activated as outputs, establishing a particular (zero or non-zero) voltage across sensor capacitor 20 and a particular (e.g., non-zero) current through resistor 40. But in this embodiment, the voltage at of pins 21, 41, and 61 may not all be the same, and the voltage at pins 41 and 61 may not be the same. In some embodiments, the voltage at pin 41 may always be different than the voltage at the one of pins 21, 31, and 51 that is activated. In other words, if the voltage at pin 41 is the first voltage, then the voltage at pin 21, 31, or 51 (whichever is activated) may be the second voltage, or vice versa.

The next step shown in method 300 is to release the voltage across the capacitor (step 315), for example, capacitor 20. This may be accomplished, for instance, by deactivating pin 61 as an output or placing pin 61 into a high-impedance state or a state in which pin 61 is not tied or driven to a particular voltage through microprocessor 10. In some embodiments, pin 61 may be simultaneously activated as an input or placed in an input state, for example, as described below with reference to step 320. In the embodiment illustrated, this step of releasing the voltage across the capacitor (step 315), in this example, capacitor 20, will result in sensor capacitor 20 and resistor 40 forming a series circuit with a current through sensor capacitor 20 and resistor 40 that starts at a highest value and decays asymptotically to zero (if given enough time). In this example, during this decay, the potential across sensor capacitor 20 will change, starting either at zero or at another voltage applied in step 305, for example, the difference between the first voltage and the second voltage, and ending (if given enough time) either at the difference between the first voltage and the second voltage or at zero. During this same decay, the charge of sensor capacitor 20 will change, and sensor capacitor 20 will either charge or discharge, depending on the voltages that were initially used.

In the embodiment illustrated, method 300 also includes the step of measuring the time to reach a threshold voltage (step 320). In some embodiments, this threshold voltage may be measured across the capacitor, for example, sensor capacitor 20. Thus, the voltage of pin 61 may be measured in comparison to the voltage of pin 21. In other embodiments, the voltage of pin 61 may be measured in comparison to the voltage of pin 41, or in comparison to the first voltage or second voltage described herein, for example. To measure this voltage, a pin of microchip or microprocessor 10 may be activated as an input, for example, to comparator 12. In the embodiment illustrated in FIG. 1, pin 61 may be activated as the input, but in other embodiments, another pin may be used for this purpose, which may be common to some or all of the capacitors, for example, capacitors 20, 30, and 50 of apparatus 5. The threshold voltage may be detected or measured, for example, with comparator 12, and the time may be measured, for example, with timer 14, which may be controlled by microprocessor 10, all illustrated in FIG. 1. In embodiments where the pins (for example, pins 21, 41, and 61) were driven in steps 305 and 310 to a first voltage and a second voltage, the threshold voltage may be between the first voltage and the second voltage.

The threshold voltage (or voltages) may be generated in some embodiments by microprocessor 10. In other embodiments, the threshold voltage(s) may be externally generated and input to microprocessor 10, comparator 12, or both. In a number of embodiments, pins 21, 31, 41, 51, and 61 are either at the first voltage, at the second voltage, or in a high-impedance state. In the embodiment illustrated, when pins 21, 31, 41, or 51 are in a high-impedance state, their voltage may be equal to that of pin 61.

In various embodiments, the time to reach the threshold voltage is measured (step 320) from the time that the voltage across the capacitor is released (step 315). In other embodiments, the time to reach the threshold voltage is measured (step 320) from the time that the voltage across the capacitor reaches a starting voltage. This starting voltage may be, for example, between the voltage applied across the capacitor in step 305 and the threshold voltage. In other embodiments, current may be measured instead of (or in addition to) voltage. In some embodiments in which current is measured, step 320 may be replaced with a step of measuring a time to reach a threshold current. In some embodiments in which current is measured, time may be measured from the time that the current through the capacitor reaches a starting current. In various embodiments, the time may be measured from a particular current to a particular voltage, or from a particular voltage to a particular current. In some embodiments, current and voltage may be measured, and the energy or charge stored in the capacitor, or the change in energy or charge in the capacitor may be calculated. In some embodiments, the time to change the charge in the capacitor may be measured by calculating charge using both current and voltage.

In the description of method 300 above, sensor capacitor 20 is described as an example of the capacitor of steps 305 and 315. However, in many embodiments, the measuring of the time to reach a threshold voltage (step 320) or a corresponding step, is repeated (step 325) for one, two, or more reference capacitors, for example, reference capacitors 30 and 50 shown in FIG. 1. This concept was introduced above with reference to steps 210, 225, and 240 of method 200 illustrated in FIG. 2. In subsequent iterations of method 300, pin 31 or pin 51 is activated in step 305 rather than pin 21. Pin 21 may be deactivated in a high-impedance state when one of pins 31 and 51 is activated for steps 305, 310, and 315. In many embodiments, only one of pins 21, 31, and 51 is activated as an output at a time, the others being deactivated in a high-impedance state. In this manner, microprocessor 10 can dynamically reconfigure a number of charge or discharge circuits to control the charge or discharge of one capacitor at a time through a common resistor. In various embodiments, the same resistor 40, comparator 12, timer 14, microprocessor 10, software, first voltage, second voltage, threshold voltage, pin 41, pin 61, conductors, or a combination thereof, may be used for the different capacitors, for example, capacitors 20, 30, and 50. In some embodiments, pin 41 to resistor 40 may be activated as an output and driven to essentially the same particular voltage while steps 305, 315, and 320 are applied to the different capacitors. Thus, the step of establishing a current through the resistor (step 310) may be accomplished by activating pin 61 as an output.

In different embodiments, the capacitors may be cycled through steps 305 to 310 in different orders. In many embodiments, essentially the same voltage may be applied across the two, three, or more capacitors, (for example, capacitors 20, 30, and 50) in step 305. In many embodiments, it is more important that that voltage be the same for the different capacitors than that the voltage be precisely a particular value. This characteristic allows certain embodiments of the invention to be well suited to being powered by a battery, where voltage may decrease over time, but any changes in voltage would be negligible from one iteration of steps 305 to 320 to the next. The same is true for the threshold voltage of step 320 in many embodiments. Similarly, in many embodiments, it is more important that that threshold voltage be the same for the different capacitors than that the threshold voltage be precisely a particular value.

As illustrated, method 300 of FIG. 3 may also include the step of calculating the capacitance of one capacitor (step 250), for example, the first capacitor or sensor capacitor 20. This may be the same as step 250 of method 200 described above with reference to FIG. 2, for example.

In various embodiments, method 200, method 300 or other methods in accordance with the invention may be repeated and the capacitance of the first capacitor may be recalculated using new measurements for some or all capacitors. Method 300 is illustrated as repeating (step 330), which may include repeating the steps 305 to 325 for each of the capacitors. In other embodiments, just the measurements for the sensor capacitor 20 may be repeated, or the measurements for sensor capacitor 20 may be repeated more often than the measurements for the reference capacitor or capacitors 30, 50, or both. Such methods may be repeated, for example, to provide information from a sensor capacitor in essentially real time, for example, to show how the parameter varies over time, or to provide current information regarding that parameter. In some embodiments, a number of readings may be obtained and then averaged to obtain greater accuracy, for instance. In some embodiments, outliers may be discarded in such averaging.

Method 200 or 300 may be repeated, in certain embodiments, alternating between charging (increasing the potential from a lower potential to a higher potential) and discharging (decreasing the potential from a higher potential to a lower potential) across the capacitors. As an example related to method 200, in particular embodiments, the steps of measuring a time to change the charge of the first capacitor (step 210), measuring a time to change the charge of the second capacitor (step 225), and measuring a time to change the charge, of the third capacitor (step 240) are repeated, alternating between charging and discharging the first, second, and third capacitors. Alternating between charging and discharging, and averaging or comparing the results, may eliminate certain sources of error, for example, when calculating the capacitance of the first capacitor (step 250), for instance, sensor capacitor 20.

In some embodiments, different threshold voltages may be used depending on whether a capacitor is being charged or discharged. For example, two different threshold voltages, may be used between the first voltage and the second voltage, for instance, a first threshold voltage and a second threshold voltage. Particular embodiments may include measuring a first time for sensor capacitor 20 to change from the first voltage to a first threshold voltage, measuring a second time for first reference capacitor 30 to change from the first voltage to the first threshold voltage, and using at least the first time, the second time, and a capacitance of first reference capacitor 30, calculating a capacitance of sensor capacitor 20. Microprocessor 10 may be configured to perform these steps, and may use timer 14 for time measurements. Such embodiments that have a second reference capacitor 50, may include measuring a third time for second reference capacitor 50 to change from the first voltage to the first threshold voltage, and using at least the first time, the second time, the third time, the capacitance of the first reference capacitor 30, and the capacitance of second reference capacitor 50, calculating the capacitance of sensor capacitor 20.

In a particular embodiment, the first voltage is lower than the second voltage. The capacitors (e.g., 20 and 30, and in some embodiments, 50) are alternately charged and the time to charge is measured (e.g., steps 210, 225, 240, and 320) from the first voltage to a first threshold voltage. The first threshold voltage may be between the first voltage and the second voltage and the first threshold voltage may be closer to the second voltage than to the first voltage. For instance, the first threshold voltage may be about 70 percent of the way from the first voltage to the second voltage. Next, the capacitors (e.g., 20 and 30, and in some embodiments, 50) are alternately charged to the second voltage, and are then discharged while the time to discharge each capacitor is measured (e.g., steps 210, 225, 240, and 320) from the second voltage to a second threshold voltage. The second threshold voltage may be between the first voltage and the second voltage and the second threshold voltage may be closer to the first voltage than to the second voltage. For instance, the second threshold voltage may be about 30 percent of the way from the first voltage to the second voltage.

The detailed description of examples of embodiments herein makes reference to the accompanying drawings, which show examples of embodiments by way of illustration and its best mode. While these examples of embodiments are described in sufficient detail to enable those skilled in the art to practice the invention, it should be understood that other embodiments may be realized and that logical changes may be made without departing from the spirit and scope of the invention. Thus, the detailed description herein is presented for purposes of illustration only and not of limitation. For example, unless stated otherwise, the steps recited in the method or process descriptions may be executed in any order and are not limited to the order presented.

Further, benefits, other advantages, and solutions to problems have been described herein with regard to specific embodiments. However, the benefits, advantages, solutions to problems, and element(s) that may cause benefit, advantage, or solution to occur or become more pronounced are not to be construed as critical, required, or essential features or elements of the claims or the invention. Reference to an element in the singular is not intended to mean "one and only one" unless explicitly so stated, but rather "one or more." As used herein, the terms "comprises", "comprising", or a variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical".

What is claimed is:

1. An apparatus for measuring a parameter, the apparatus comprising:
   a microprocessor having a plurality of pins;
   a sensor capacitor configured to change capacitance as the parameter changes, the sensor capacitor having a first lead electrically connected to a first pin of the microprocessor, and a second lead electrically connected to a second pin of the microprocessor;
   a first reference capacitor having a first lead electrically connected to a third pin of the microprocessor, and a second lead electrically connected to the second pin of the microprocessor;
   a resistor having a first lead electrically connected to a fourth pin of the microprocessor, and a second lead electrically connected to the second pin of the microprocessor;
   a second reference capacitor having a first lead electrically connected to a fifth pin of the microprocessor, and a second lead electrically connected to the second pin of the microprocessor a comparator configured to detect whether a threshold voltage has been reached;
a timer, wherein the apparatus is configured to use the timer to measure how long it takes for:
the sensor capacitor to reach the threshold voltage;
the first reference capacitor to reach the threshold voltage; and
the second reference capacitor to reach the threshold voltage;
wherein the sensor capacitance is calculated using the formula:

Sensor Capacitance=[(TimerS−Timer1)/(Timer2−Timer1)](Ref2−Ref1)+Ref1 wherein:
TimerS is the time for the sensor capacitor to reach the threshold voltage,
Timer1 is the time for the first reference capacitor to reach the threshold voltage,
Timer2 is the time for the second reference capacitor to reach the threshold voltage,
Ref1 is the capacitance of the first reference capacitor, and
Ref2 is the capacitance of the second reference capacitor.

2. The apparatus of claim 1 wherein the parameter is a measure of the relative presence of a substance.

3. The apparatus of claim 1 wherein the parameter comprises humidity.

4. The apparatus of claim 1 wherein the parameter comprises pressure.

5. The apparatus of claim 1 wherein the parameter comprises force.

6. The apparatus of claim 1 wherein the parameter comprises acceleration.

7. The apparatus of claim 1 wherein the parameter comprises at least one of proximity and displacement.

8. The apparatus of claim 1 further comprising software configured to control the microprocessor so that at least the first pin, the third pin, and the fifth pin are alternately activated and when not activated, are left in a high-impedance state.

9. The apparatus of claim 1 further comprising software configured to control the microprocessor so that at least the first pin, the third pin, and the fifth pin are alternately activated and when activated, are driven as outputs to one of a first voltage and a second voltage.

10. The apparatus of claim 1 further comprising software configured to control the microprocessor so that the second pin is alternately activated as an output and as an input to a comparator, and when activated as an output, is driven to one of a first voltage and a second voltage.

11. A method of measuring the capacitance of a first capacitor, the method comprising the steps of:
activating at least a first pin of a microprocessor, wherein the first pin is electrically connected to the first capacitor;
while the first pin is activated, measuring a time to change the charge of the first capacitor;
after the measuring of the time to change the charge of the first capacitor, deactivating the first pin into a high impedance state;
activating at least a second pin of the microprocessor, wherein the second pin is electrically connected to a second capacitor;
while the second pin is activated, measuring a time to change the charge of the second capacitor;
after the measuring of the time to change the charge of the second capacitor, deactivating the second pin into a high impedance state;
activating at least a third pin of the microprocessor, wherein the third pin is electrically connected to a third capacitor;
while the third pin is activated, measuring a time to change the charge of the third capacitor;
after the measuring of the time to change the charge of the third capacitor, deactivating the third pin into a high impedance state; and
using at least the time to change the charge of the first capacitor, the time to change the charge of the second capacitor, and the time to change the charge of the third capacitor to calculate the capacitance of the first capacitor;
wherein the second capacitor and third capacitor are reference capacitors having known capacitances and the step of calculating the capacitance of the first capacitor includes finding the difference in capacitance between the second capacitor and the third capacitor.

12. The method of claim 11 wherein the step of measuring of the time to change the charge of the first capacitor includes detecting when a threshold voltage is reached and measuring the time to reach the threshold voltage.

13. The method of claim 11 wherein the steps of measuring a time to change the charge of the first capacitor, measuring a time to change the charge of the second capacitor, and measuring a time to change the charge of the third capacitor are repeated, in any order, alternating between charging and discharging the first, second, and third capacitors.

14. The method of claim 11 wherein the step of calculating the capacitance of the first capacitor includes adding the capacitance of the second capacitor.

15. The method of claim 11 the step of calculating the capacitance of the first capacitor includes finding the difference between the time to change the charge of the first capacitor and the time to change the charge of the second capacitor.

16. A method of measuring the capacitance of a first capacitor, the method comprising the steps of:
activating at least a first pin of a microprocessor, wherein the first pin is electrically connected to the first capacitor;
while the first pin is activated, measuring a time to change the charge of the first capacitor;
after the measuring of the time to change the charge of the first capacitor, deactivating the first pin into a high impedance state;
activating at least a second pin of the microprocessor, wherein the second pin is electrically connected to a second capacitor;
while the second pin is activated, measuring a time to change the charge of the second capacitor;
after the measuring of the time to change the charge of the second capacitor, deactivating the second pin into a high impedance state;
activating at least a third pin of the microprocessor, wherein the third pin is electrically connected to a third capacitor;
while the third pin is activated, measuring a time to change the charge of the third capacitor;
after the measuring of the time to change the charge of the third capacitor, deactivating the third pin into a high impedance state; and
using at least the time to change the charge of the first capacitor, the time to change the charge of the second capacitor, and the time to change the charge of the third capacitor to calculate the capacitance of the first capacitor;

wherein the second capacitor and third capacitor are reference capacitors having known capacitances and the step of calculating the capacitance of the first capacitor includes adding the capacitance of the second capacitor.

17. The method of claim 16 wherein the step of measuring of the time to change the charge of the first capacitor includes detecting when a threshold voltage is reached and measuring the time to reach the threshold voltage.

18. The method of claim 16 wherein the steps of measuring a time to change the charge of the first capacitor, measuring a time to change the charge of the second capacitor, and measuring a time to change the charge of the third capacitor are repeated, in any order, alternating between charging and discharging the first, second, and third capacitors.

19. A method of measuring the capacitance of a first capacitor, the method comprising the steps of:
  activating at least a first pin of a microprocessor, wherein the first pin is electrically connected to the first capacitor;
  while the first pin is activated, measuring a time to change the charge of the first capacitor;
  after the measuring of the time to change the charge of the first capacitor, deactivating the first pin into a high impedance state;
  activating at least a second pin of the microprocessor, wherein the second pin is electrically connected to a second capacitor;
  while the second pin is activated, measuring a time to change the charge of the second capacitor;
  after the measuring of the time to change the charge of the second capacitor, deactivating the second pin into a high impedance state;
  activating at least a third pin of the microprocessor, wherein the third pin is electrically connected to a third capacitor;
  while the third pin is activated, measuring a time to change the charge of the third capacitor;
  after the measuring of the time to change the charge of the third capacitor, deactivating the third pin into a high impedance state; and
  using at least the time to change the charge of the first capacitor, the time to change the charge of the second capacitor, and the time to change the charge of the third capacitor to calculate the capacitance of the first capacitor;
  wherein the step of calculating the capacitance of the first capacitor includes finding the difference between the time to change the charge of the first capacitor and the time to change the charge of the second capacitor.

20. The method of claim 19 wherein the step of measuring of the time to change the charge of the first capacitor includes detecting when a threshold voltage is reached and measuring the time to reach the threshold voltage.

21. The method of claim 19 wherein the steps of measuring a time to change the charge of the first capacitor, measuring a time to change the charge of the second capacitor, and measuring a time to change the charge of the third capacitor are repeated, in any order, alternating between charging and discharging the first, second, and third capacitors.

22. A method of measuring the capacitance of a first capacitor, the method comprising the steps of:
  activating at least a first pin of a microprocessor, wherein the first pin is electrically connected to the first capacitor;
  while the first pin is activated, measuring a time to change the charge of the first capacitor;
  after the measuring of the time to change the charge of the first capacitor, deactivating the first pin into a high impedance state;
  activating at least a second pin of the microprocessor, wherein the second pin is electrically connected to a second capacitor;
  while the second pin is activated, measuring a time to change the charge of the second capacitor;
  after the measuring of the time to change the charge of the second capacitor, deactivating the second pin into a high impedance state;
  activating at least a third pin of the microprocessor, wherein the third pin is electrically connected to a third capacitor;
  while the third pin is activated, measuring a time to change the charge of the third capacitor;
  after the measuring of the time to change the charge of the third capacitor, deactivating the third pin into a high impedance state; and
  using at least the time to change the charge of the first capacitor, the time to change the charge of the second capacitor, and the time to change the charge of the third capacitor to calculate the capacitance of the first capacitor;
  wherein the step of calculating the capacitance of the first capacitor includes finding the difference between the time to change the charge of the second capacitor and the time to change the charge of the third capacitor.

23. The method of claim 22 wherein the step of measuring of the time to change the charge of the first capacitor includes detecting when a threshold voltage is reached and measuring the time to reach the threshold voltage.

24. The method of claim 22 wherein the steps of measuring a time to change the charge of the first capacitor, measuring a time to change the charge of the second capacitor, and measuring a time to change the charge of the third capacitor are repeated, in any order, alternating between charging and discharging the first, second, and third capacitors.

25. A method of measuring the capacitance of a first capacitor, the method comprising the steps of:
  activating at least a first pin of a microprocessor, wherein the first pin is electrically connected to the first capacitor;
  while the first pin is activated, measuring a time to change the charge of the first capacitor;
  after the measuring of the time to change the charge of the first capacitor, deactivating the first pin into a high impedance state;
  activating at least a second pin of the microprocessor, wherein the second pin is electrically connected to a second capacitor;
  while the second pin is activated, measuring a time to change the charge of the second capacitor;
  after the measuring of the time to change the charge of the second capacitor, deactivating the second pin into a high impedance state;
  activating at least a third pin of the microprocessor, wherein the third pin is electrically connected to a third capacitor;
  while the third pin is activated, measuring a time to change the charge of the third capacitor;
  after the measuring of the time to change the charge of the third capacitor, deactivating the third pin into a high impedance state; and using at least the time to change the charge of the first capacitor, the time to change the charge of the second capacitor, and the time to change the charge of the third capacitor to calculate the capacitance of the first capacitor;

wherein the step of calculating the capacitance of the first capacitor includes finding the difference between the time to change the charge of the first capacitor and the time to change the charge of the second capacitor, and dividing this quantity by the difference between the time to change the charge of the second capacitor and the time to change the charge of the third capacitor.

26. The method of claim 25 wherein the step of measuring of the time to change the charge of the first capacitor includes detecting when a threshold voltage is reached and measuring the time to reach the threshold voltage.

27. The method of claim 25 wherein the steps of measuring a time to change the charge of the first capacitor, measuring a time to change the charge of the second capacitor, and measuring a time to change the charge of the third capacitor are repeated, in any order, alternating between charging and discharging the first, second, and third capacitors.

28. A method of measuring the capacitance of a first capacitor, the method comprising the steps of:
    activating at least a first pin of a microprocessor, wherein the first pin is electrically connected to the first capacitor;
    while the first pin is activated, measuring a time to change the charge of the first capacitor;
    after the measuring of the time to change the charge of the first capacitor, deactivating the first pin into a high impedance state;
    activating at least a second pin of the microprocessor, wherein the second pin is electrically connected to a second capacitor;
    while the second pin is activated, measuring a time to change the charge of the second capacitor;
    after the measuring of the time to change the charge of the second capacitor, deactivating the second pin into a high impedance state;
    activating at least a third pin of the microprocessor, wherein the third pin is electrically connected to a third capacitor;
    while the third pin is activated, measuring a time to change the charge of the third capacitor;
    after the measuring of the time to change the charge of the third capacitor, deactivating the third pin into a high impedance state; and
    using at least the time to change the charge of the first capacitor, the time to change the charge of the second capacitor, and the time to change the charge of the third capacitor to calculate the capacitance of the first capacitor;
    wherein the step of calculating the capacitance of the first capacitor comprises using the formula:

Sensor Capacitance=[(TimerS−Timer1)/(Timer2−Timer1)](Ref2−Ref1)+Ref1 wherein:
        TimerS is the time to change the charge of the first capacitor,
        Timer1 is the time to change the charge of the second capacitor,
        Timer2 is the time to change the charge of the third capacitor,
        Ref1 is the capacitance of the second capacitor, and
        Ref2 is the capacitance of the third capacitor.

29. The method of claim 28 wherein the step of measuring of the time to change the charge of the first capacitor includes detecting when a threshold voltage is reached and measuring the time to reach the threshold voltage.

30. The method of claim 28 wherein the steps of measuring a time to change the charge of the first capacitor, measuring a time to change the charge of the second capacitor, and measuring a time to change the charge of the third capacitor are repeated, in any order, alternating between charging and discharging the first, second, and third capacitors.

31. A method of converting the variable capacitance output of a sensor capacitor into a digital format, the method comprising the steps of:
    using a microprocessor, without the use of intermediate switching components, forming a circuit to facilitate changing the charge of the sensor capacitor;
    using the microprocessor, without the use of intermediate switching components, changing the charge of the sensor capacitor while measuring the time required to change the charge of the sensor capacitor;
    using the microprocessor, without the use of intermediate switching components, reconfiguring the circuit to facilitate changing the charge of a first reference capacitor;
    using the microprocessor, without the use of intermediate switching components, changing the charge of the first reference capacitor while measuring the time required to change the charge of the first reference capacitor;
    using the microprocessor, without the use of intermediate switching components, reconfiguring the circuit to facilitate changing the charge of a second reference capacitor;
    using the microprocessor, without the use of intermediate switching components, changing the charge of the second reference capacitor while measuring the time required to change the charge of the second reference capacitor; and
    using the microprocessor and at least the time required to change the charge of the sensor capacitor, the time required to change the charge of the first reference capacitor, and the time required to change the charge of the second reference capacitor to calculate a digital output that is dependent upon the capacitance of the sensor capacitor; and
    wherein the step of calculating a digital output comprises using the formula:

Sensor Capacitance=[(TimerS−Timer1)/(Timer2−Timer1)](Ref2−Ref1)+Ref1 wherein:
        TimerS is the time to change the charge of the sensor capacitor,
        Timer1 is the time to change the charge of the first reference capacitor,
        Timer2 is the time to change the charge of the second reference capacitor,
        Ref1 is the capacitance of the first reference capacitor, and
        Ref2 is the capacitance of the second reference capacitor.

32. The method of claim 31 wherein the steps of changing the charge of the sensor capacitor, changing the charge of the first reference capacitor, and changing the charge of the second reference capacitor are all accomplished by passing current through a common resistor electrically connected to the microprocessor without any intermediate switching components there between.

33. The method of claim 31 wherein the steps of changing the charge of the sensor capacitor, changing the charge of the first reference capacitor, and changing the charge of the second reference capacitor are all accomplished by changing the charge from a common first voltage to a common threshold voltage.

34. The method of claim 31 wherein the changing the charge of the sensor capacitor and the changing the charge of the first reference capacitor are repeated, alternating between changing from a lower potential to a higher potential, and changing from a higher potential to a lower potential.

* * * * *